United States Patent [19]
Thornton

[11] Patent Number: 4,685,460
[45] Date of Patent: Aug. 11, 1987

[54] SKIN CLIP REMOVER

[75] Inventor: Curtis W. Thornton, Raleigh, N.C.

[73] Assignee: Edward Weck & Company, Inc., Research Triangle Park, N.C.

[21] Appl. No.: 291,534

[22] Filed: Aug. 10, 1981

[51] Int. Cl.$^4$ ............................................. A61B 17/10
[52] U.S. Cl. ........................................ 128/321; 254/28
[58] Field of Search ................. 128/321, 323; 254/28; 227/63; 81/416; 16/DIG. 13, 225

[56] References Cited

U.S. PATENT DOCUMENTS 2,202,984  6/1940  Drypolcher .......................... 254/28
3,156,756 11/1964  Seaver .................................. 16/225 X
4,026,520  5/1977  Rothfuss et al. ....................... 254/28

Primary Examiner—Michael H. Thaler
Attorney, Agent, or Firm—Lawrence S. Levinson; Robert E. Lee, Jr.

[57] ABSTRACT

A skin clip remover for removing skin clips or staples which have been placed into the skin across a wound to close and retain the wound in a closed and healing position comprises a handle element and a trigger element joined together at a pivot point to form a hand operated tool capable of gripping and deforming the crown of a skin clip when the proximal ends of the two elements are forced toward each other to bring together into such gripping and deforming attitude the opposing faces of the distal ends of such two elements which are in the form of a pair of parallel anvil feet at an obtuse angle on the distal end of the handle element and a hawk bill projection at an obtuse angle on the distal end of the trigger element, such obtuse angles opposing each other to form a diamond shaped pocket to entrap the crown of a skin clip for deformation and removal.

2 Claims, 13 Drawing Figures

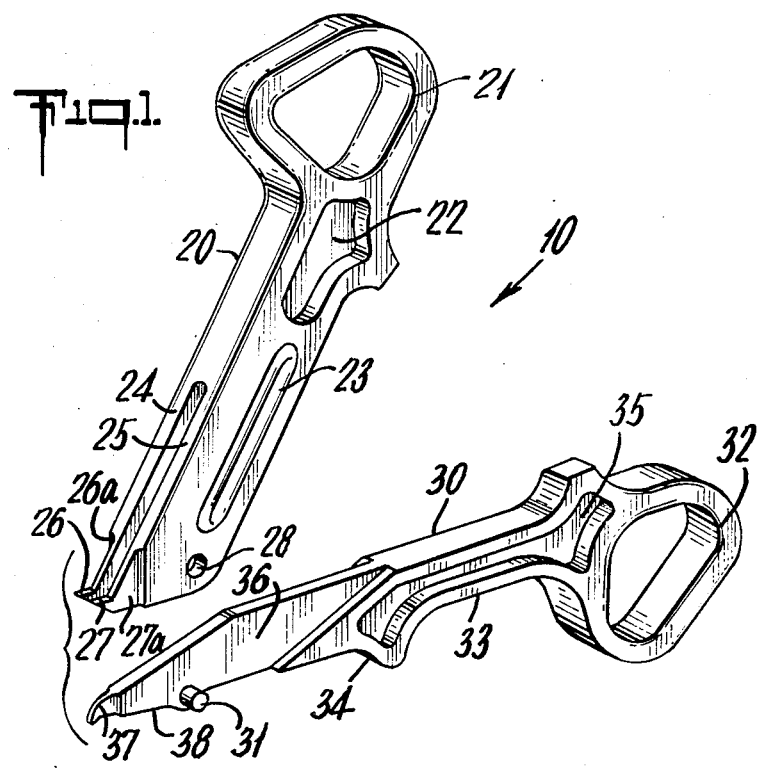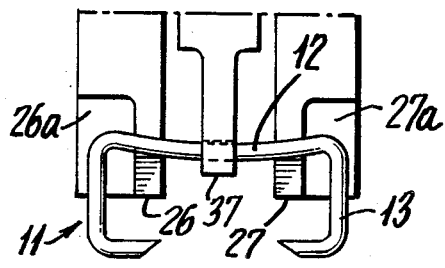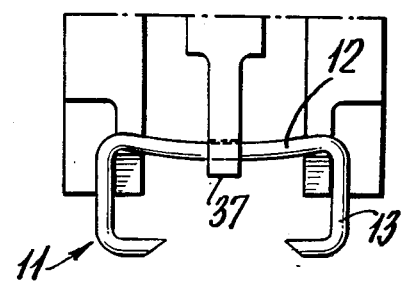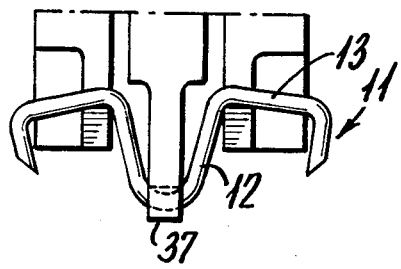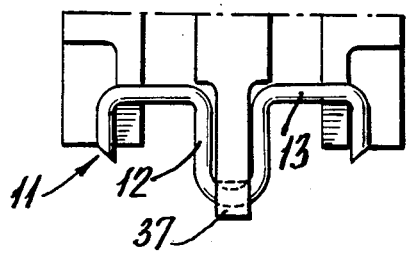

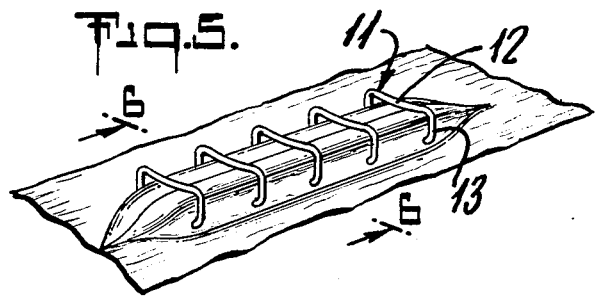
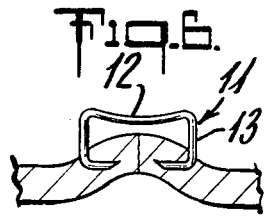
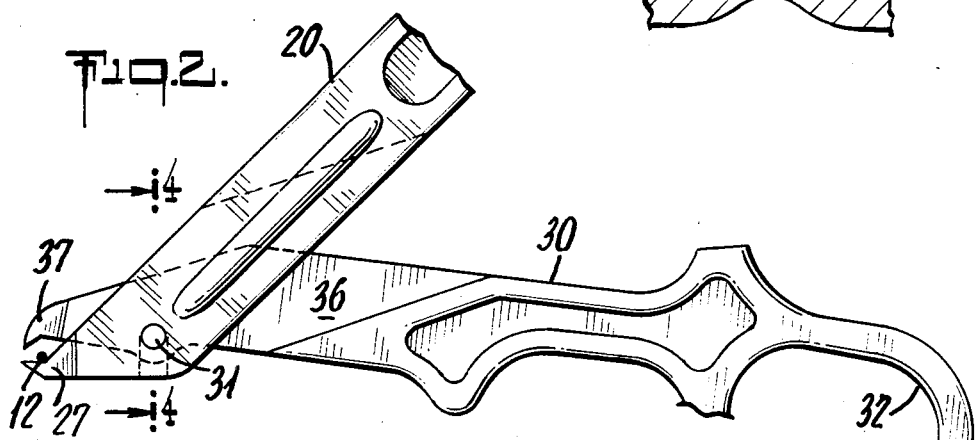
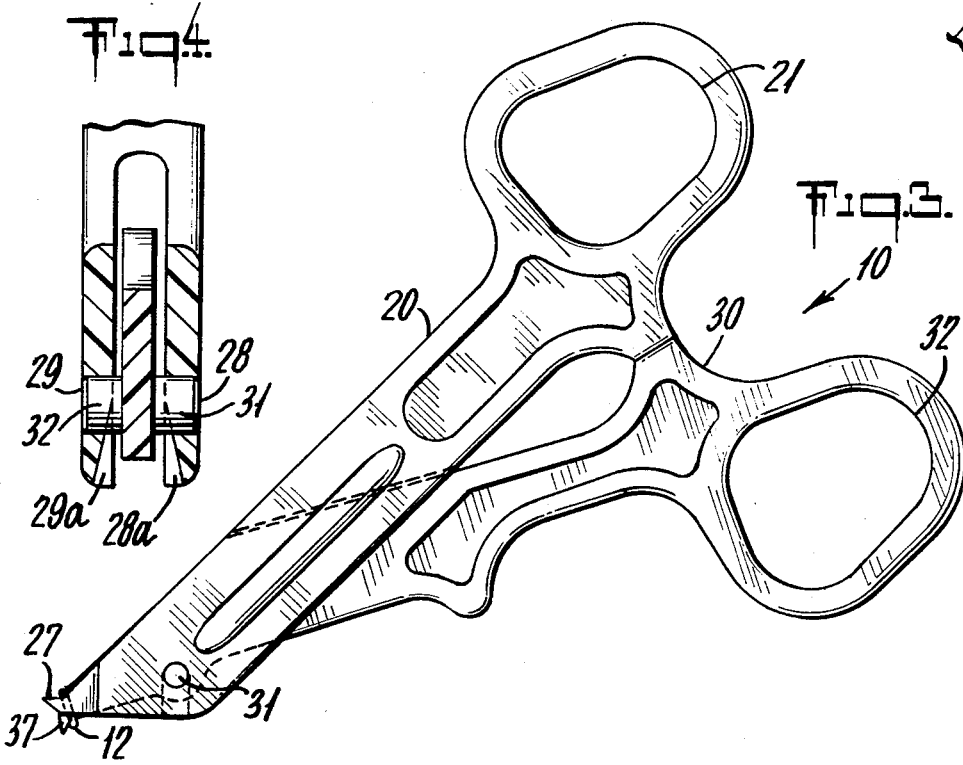

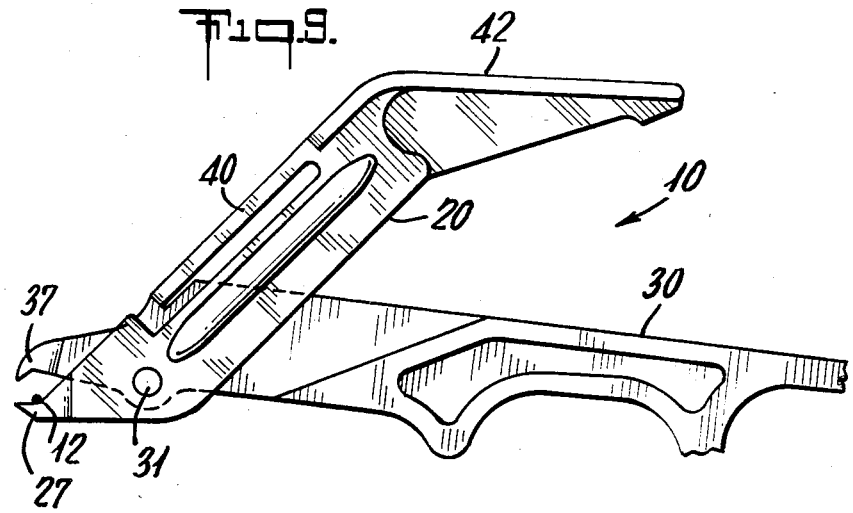
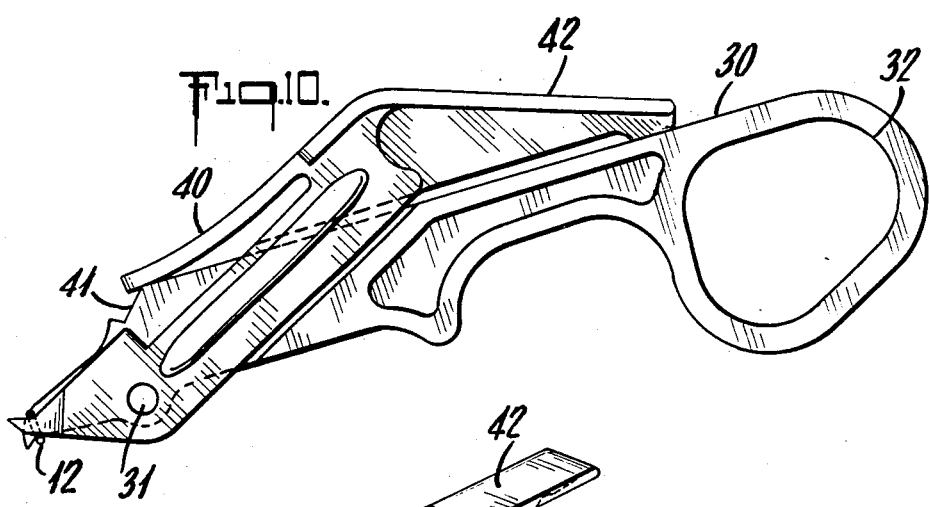
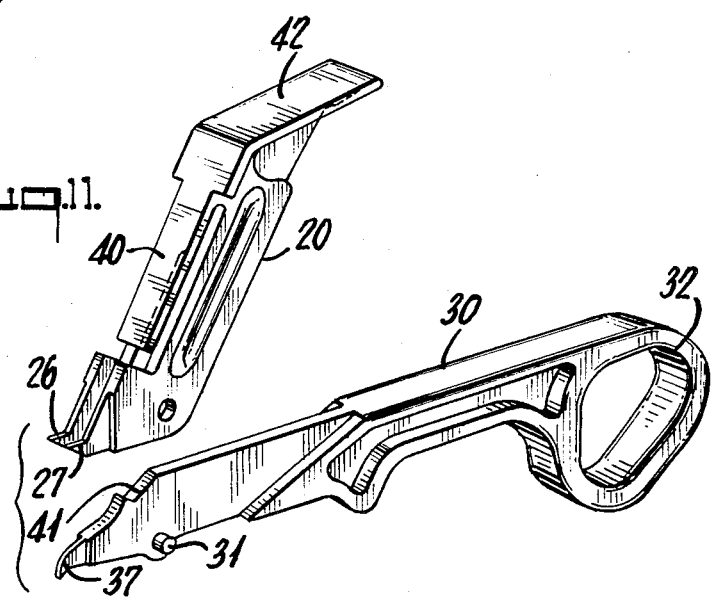

SKIN CLIP REMOVER

FIELD OF THE INVENTION

This invention relates to a skin clip remover useful for removing skin clips or staples which have been placed ,into the skin across a wound to close and retain the wound in a closed and healing position.

BACKGROUND OF THE INVENTION

With the development of stapling devices, or skin clip appliers, particularly suited for surgical use, and the consequent speed with which incision or wound closure can be accomplished by a surgeon with such devices as compared to use of thread suture materials with needles requiring time-consuming tying of the suture material, it has become more and more common for a surgeon to choose skin clips or staples for incision or wound closures. U.S. Pat. Nos. 3,643,851, 3,717,294 and 4,014,492 are representative of disclosures of surgical staplers, or skin clip appliers, and of surgical staples, or skin clips.

When staples, or skin clips are used for incision or wound closure, they are removed when the healing process has sufficiently progressed, or at such other time as the attending surgeon determines that removal is desirable. A number of removal tools, or extractors, are available. See, for example, U.S. Pat. No. 4,026,520 which discloses an extractor specifically designed for removal of surgical staples, or U.S. Pat. No. 2,202,984 which discloses a staple remover, originally intended for removal of staples from paper or like material, which could be used to remove surgical staples. However, many present removal tools cause a substantial amount of tissue damage, with consequent patient trauma, when the surgical staples, or skin clips, are being removed.

BRIEF SUMMARY

The substantially atraumatic skin clip remover of the present invention overcomes disadvantages of prior skin clip, or surgical staple, removers and makes removal of a skin clip from a skin clip closed incision or wound site with a minimum of tissue disturbance or damage, and consequently, a minimum of patient trauma. This is particularly so when the skin clip is of the configuration disclosed in U.S. patent application Ser. No. 227,569, filed Jan. 22, 1981, now U.S. Pat. No. 4,375,866, and such skin clip has been applied by the skin clip applier disclosed and claimed in said U.S. patent application Ser. No. 227,569. As explained in that U.S. patent application, the skin clips have a shape, when deformed into place as an incision or wound closing element by the skin clip applier described in that U.S. patent application, which makes removal easier for the surgeon and less traumatic to the patient. The specific advantages of the present skin clip remover as compared to prior devices will be explained more fully in the following detailed description of illustrative embodiments of the invention.

The skin clip remover of this invention is formed of a combination of a handle element and a trigger element which are joined together at a pivot point to form a hand operated tool capable of gripping an object, e.g., the crown of a skin clip, between the opposing faces of the distal ends of the handle element and the trigger element when the proximal ends of these two elements are forced toward each other by action of the hand in which these proximal ends are held. The distal end of the handle element is split to form two parallel sections terminating in two parallel anvil feet which are formed at an obtuse angle to the general longitudinal axis of the handle element. These two parallel sections including the two parallel anvil feet are spaced to permit passage therebetween of the distal end of the trigger element which terminates in a hawk bill formed at an obtuse angle to the general longitudinal axis of the trigger element opposing the angle of the two anvil feet.

The hawk bill at the distal end of the trigger element together with the two anvil feet of the split distal end of the handle element create a diamond shaped pocket which entraps the crown of a skin clip when the anvil feet are first inserted between the crown of the implanted skin clip and the patient's skin, and the hawk bill is then brought into contact with the crown of the skin clip by the action of the trigger. The positive locking action provided by the hawk bill distal end on the trigger element serves to accurately position the crown of the skin clip for proper deformation. To make certain that deformation can not take place before the crown of the skin clip is located in the diamond shaped pocket created by the hawk bill and the anvil feet, the trigger element is preferably formed so that the angle of approach to the hawk bill is at a slight angle away from the line of contact surface of the anvil feet.

The most desirable extraction of a skin clip from placement in a wound closure is one wherein each of the legs of the skin clip is withdrawn through the same arcuate path by which such leg entered the tissue at the time of placement, i.e., the legs are withdrawn through the same holes made by the legs when the skin clip was applied, and consequently, without tearing and with minimum disturbance to the tissue surrounding such holes, i.e., with the least trauma to the patient.

In a preferred embodiment of skin clip remover of this invention, a superior extraction configuration is achieved by providing a pivot between the handle element and the trigger element which does not restrain the lateral outward movement of the two parallel sections of the split distal end of the handle element terminating in the two anvil feet as a deforming load is applied by the contact surface of the hawk bill distal end of the trigger element to the crown of a skin clip entrapped between the anvil feet and the hawk bill. This freedom of the anvil feet to move apart, or splay, during the deformation of the crown of a skin clip in the process of extraction has the advantage of better distribution of the deforming load on the crown of the skin clip which results in a more symetrical pattern of deformation of the crown and a consequent superior extraction path of the legs of the skin clip for atraumatic removal. Because of this splaying freedom of the anvil feet, the overall width of the pair of anvil feet, i.e., from outside edge of one to outside edge of the other, when not under deforming load can be reduced to fit easily within the crown of the skin clip, thus making it easier for the surgeon to insert the anvil feet under the crown and less traumatic for the patient. As a deforming load is aoplied to the crown of the skin clip, the anvil feet will splay to the ends of the crown and be retained there by the bend at each end of the crown. No matter at what position under the crown the anvil feet are inserted, each, deformation of a crown will be substantially identical with deformations of other crowns because the anvil feet will position themselves at the ends of a crown before actual deformation takes place. The splaying of the anvil feet to the ends of a crown better distributes the deforming load and, as deformation proceeds, the anvil feet are free to return inwardly as the crown is bent and then outwardly again to support the legs as they are withdrawn. This will be explained in more detail hereinafter.

The skin clip remover of the present invention is most advantageously used for removing skin clips of the shape formed by the skin clip applier of the U.S. patent application Ser. No. 227,569 referred to hereinbefore. As noted therein, the crowns of the skin clips in a wound closing placement do not touch the wound and are bowed downwardly to a slight extent. Both of these characteristics are helpful because less difficulty is experienced in placing the anvil feet under the crown of the skin clip to be removed and less energy is required to accomplish the deformation necessary for removal of the skin clip.

BRIEF DESCRIPTION OF DRAWINGS

The skin clip remover of this invention will be described in more detail with reference to the accompanying drawings which show illustrative embodiments of the invention.

In the drawings:

FIG. 1 is a perspective and exploded view showing the relation of a handle element and a trigger element of one embodiment of a skin clip remover of the present invention.

FIG. 2 is a side view of the skin clip remover of FIG. 1 with the handle element and the trigger element (both of which are partly broken away) assembled and with a skin clip (in section) positioned for deformation.

FIG. 3 is a side view of the skin clip remover of FIG. 1 with the handle element and the trigger element assembled and in the fully closed position with a fully deformed skin clip (partly in section) gripped therebetween.

FIG. 4 is a partial end view of the skin clip remover of FIG. 1 partly in section taken along line 4—4 of FIG. 2 showing pivot studs of the trigger element seated in pivot holes of the handle element and showing tapered channels in handle element leading into pivot holes.

FIG. 5 is a perspective view of skin clips in place to hold a wound or an incision in a closed and healing position.

FIG. 6 is a section taken along line 6—6 of FIG. 5 showing a single skin clip in place in a closed incision or wound.

FIG. 7 is a partial end view of a skin clip remover with the handle element and the trigger element in the relative positions shown in FIG. 2 or in FIG. 9 and with a skin clip in position for deformation.

FIG. 7a is a partial end view of a skin clip remover with the handle element and the trigger element in their relative positions just after the start of deformation of the skin clip gripped therebetween.

FIG. 8 is a partial end view of a skin clip remover with the handle element and the trigger element in their, relative positions just prior to the completion of deformation of the skin clip gripped therebetween.

FIG. 8a is a partial end view of a skin clip remover with the handle element and the trigger element in their relative positions as shown in FIG. 3 or in FIG. 10 and with a fully deformed skin clip gripped therebetween.

FIG. 9 is a side view of another embodiment of a skin clip remover of the present invention with a handle element and a trigger element (part of the trigger ring broken away) assembled and with a skin clip (in section) positioned for deformation.

FIG. 10 is a side view of the skin clip remover of FIG. 9 with the handle element and the trigger element assembled and in the fully closed position with a fully deformed skin clip (partly in section) gripped therebetween.

FIG. 11 is a perspective and exploded view showing the relation of the handle element and the trigger element of the embodiment of skin clip remover shown in FIGS. 9 and 10.

DETAILED DESCRIPTION

With reference to the accompanying drawings, the same parts are identified by the same reference numerals in all figures.

In FIG. 1, a specific embodiment of the skin clip remover of the present invention is indicated generally by reference numeral 10 and includes a handle element 20 and a trigger element 30 which are shown in this exploded view in their relative positions. In FIGS. 2 and 3, the remover 10 is shown in assembled form. FIG. 2 shows the remover 10 with the handle element 20 and the trigger element 30 in positions to accept a skin clip 11 for deformation. FIG. 3 shows the remover 10 in fully closed condition with a fully deformed (extracted) skin clip 11 gripped between the two elements.

The handle element 20 (as seen in FIGS. 1, 2 and 3) is formed with a ring 21 at the proximal end to accommodate the thumb of the user in manipulating the remover 10. Identation 22 and rib 23 are optional design features to reduce the weight and increase the structural strength of the element 20 and will vary depending on overall design and material used. The distal end of handle 20 is divided into two parallel sections 24 and 25 which terminate in two parallel anvil feet 26 and 27 which are at an obtuse angle both to the top surfaces of the two parallel sections 24 and 25 and to the general longitudinal axis of the handle element 20. Pivot holes 28 and 29 (FIG. 4) are provided in the distal end of handle element 20 at the location necessary for the desired cooperation of handle element 20 and trigger element 30 which is provided with pivot studs 31 and 32.

Anvil feet 26 and 27 are preferably reduced in thickness by removing a portion of each of the parallel sections 24 and 25 as shown at 26a and 27a in order to make them more flexible, as will be explained in more detail hereinafter, and also to reduce patient discomfort when the anvil feet 26 and 27 are inserted under the crown 12 of the skin clip 11 in preparation for removal. In addition, and again to keep patient discomfort at a minimum, the anvil feet 26 and 27 are made as short as possible consistent with providing proper support for the crown 12 of the skin clip 11 while deformation is taking place.

The trigger element 30 (as seen in FIGS. 1, 2 and 3 is formed with a ring 32 at the proximal end to accommodate a finger of the user, and adjacent to such ring 32, toward the distal end, the trigger 30 is optimally and preferably contoured for two additional fingers at 33 and 34. Indentation 35 is an optional design feature to reduce weight and increase structural strength of the trigger element 30 and will vary depending on overall design and material used. The distal end of trigger element 30 is reduced in thickness to provide a portion 36 which will fit into the slot formed by the two parallel sections 24 and 25 of the handle element 20. The distal end of this portion 36 of the trigger element 30 terminates in a hawk bill projection 37 formed at an obtuse angle both to the general longitudinal axis of the trigger element 30 and to the bottom or approach surface 38 to the hawk bill 37 in a manner such that in the assembled remover 10 this obtuse angle of the hawk bill 37 opposes the obtuse angle of the two anvil feet 26 and 27 of the handle element 20. The line of the approach surface 38 to the hawk bill projection 37 is preferably angled slightly away from the line of the contact surfaces of the anvil feet 26 and 27 to ensure that the crown 12 of skin clip 11 will be properly positioned between the deforming corner of the hawk bill 37 and the deforming corners of the anvil feet 26 and 27, i.e., properly positioned in the diamond shaped pocket formed by the two deforming corners (see FIGS. 2 and 9). The length of the distal end of the portion 36 of the trigger element 30 that passes between the anvil feet 26 and 27 is reduced in thickness (see FIGS. 1 and 11) by an amount sufficient to provide clearance on each side for the crown 12 of the skin clip 11 as the crown 12 is deformed. Pivot studs 31 and 32 (FIG. 4) are provided on the two sides of the portion 36 of the distal end of trigger element 30 at the location necessary for the desired cooperation of trigger element 30 and handle element 20 which is provided with mating pivot stud holes 28 and 29.

The skin clip remover 10 shown in FIGS. 1, 2 and 3 does not include any means for biasing the remover 10 to an open position, i.e., where distal ends of handle 20 and trigger 30 are open to accept the crown 12 of a skin clip 11 (FIG. 2). Such biasing is not necessary because the remover 10 is shown as a ring handled instrument which can be readily manipulated to the desired positions by the fingers in rings 21 and 32. Of course, such a ring handled instrument can be biased to an open position if desired, for example, by a flat or coil spring in a known manner.

FIGS. 9, 10 and 11 show a preferred embodiment of the skin clip remover 10 of the present invention. In this embodiment the thumb ring 21 of the previously described embodiment (FIGS. 1, 2 and 3 has been replaced by thumb pad 42 and the handle element 20 has been biased to an open position (see FIG. 9) by the action of cantilever spring 40 in cooperation with the cam 41 on the trigger element 30. The cantilever spring 40 is shown in the form of a flat flexible bar one end of which is attached to handle element 20 at the distal end of the thumb pad 42 and the other end, i.e., the free end, mates with a notch-like cam 41 on the upper edge of the trigger element 30. Of course, other biasing arrangements can be used. The stop at the bottom of cam 41 is provided to limit movement of the handle element 20 to the desired open position. With the exception of the above described thumb pad 42 and cantilever spring 40 on the handle element 20 and the cantilever spring cam 41 on the trigger element 30, the remaining parts of this embodiment (FIGS. 9, 10 and 11) are the same as described previously in connection with FIGS. 1, 2 and 3.

The skin clip remover of this invention can be fabricated from appropriate metal, e.g., surgical grade stainless steel, or a suitable plastic, preferably an injection moldable plastic such as DELRIN 500 acetal. It can be made as a sterilizable instrument to be used many times or as a disposable instrument to be discarded after a single use.

To simplify assembly, particularly of a plastic embodiment of the skin clip remover 10 of the present invention, the pivot studs 31 and 32 may be formed as an integral part of the trigger element 30 and a pivot hole 28(29) provided in each side 25(24) of the split end of the handle element 20 with a tapered channel 28a(29a) on the inside face of each side 25(24) leading from the edge to the pivot hole 28(29) with the depth of the channels 28a and 29a decreasing from the edge to the pivot stud holes 28 and 29. Such tapered channels 28a(29a) permit the pivot studs 31 and 32 of the trigger element 30 to be forced into the pivot stud holes 28 and 29 of the handle element 20 by flexing apart the sections 24 and 25. Such "snap on" assembly operation, together with the ease and low cost of molded plastic parts manufacture, make this a prefered embodiment.

In utilizing the skin clip remover 10 of the present invention to remove a skin clip 11 from a wound closing placement (see FIGS. 5 and 6), the anvil feet 26 and 27 are inserted under the crown 12 of a skin clip 11 until the crown 12 is approximately positioned in the deforming corners of the anvil feet 26 and 27, i.e., at the base of the anvil feet 26 and 27 and against the top edges of sections 24 and 25 from which the anvil feet 26 and 27 emerge. The proximal ends of the handle element 20 and trigger element 30 are brought together by the hand of the manipulator of the remover 10 through use of the thumb ring 21 or thumb pad 42 on the proximal end of handle element 20 in combination with the ring 32, and preferable associated finger grips 33 and 34, on the proximal end of trigger element 30. The thumb pad 42 is the preferred form for the proximal end of handle element 20 because of greater ease of operation of the remover 10 which is provided by the thumb pad 42 and associated spring biasing means.

As the proximal ends of the handle element 20 and trigger element 30 approach each other, but before they actually come into contact at the end of their travel toward each other, the distal end of the trigger element 30, i.e., the hawk bill projection 37 or the approach surface 38, contacts the top of the crown 12 of the skin clip 11 and the crown 12 is relocated if necessary to the proper position for deformation in the diamond shaped pocket formed by the two deforming corners provided by the opposing obtuse angles, one formed by the anvil feet 26 and 27 projecting from the handle element 20 and the other by the hawk bill 37 projecting from the trigger element 30. This is the position shown in FIG. 7. With the crown 12 of the skin clip 11 properly positioned, deformation with consequent extraction of the skin clip 11 can proceed.

In a preferred embodiment discussed previously utilizing a pivot which does not restrain lateral outward movement of the sections 24 and 25, as deforming pressure is applied by forcing toward each other the proximal ends of handle element 20 and trigger element 30, the anvil feet 26 and 27, move outward under the crown 12 until they reach the legs 13 of skin clip 11, as shown in FIG. 7a. As deformation proceeds with an even distribution of the deforming load provided by the splayed anvil feet 26 and 27, the crown 12 is bent into the start of a U-shape with the anvil feet 26 and 27 moving inward as they are retained by the bends between the ends of crown 12 and legs 13. This is shown in FIG. 8. When the crown 12 has been deformed into a full U-shaped configuration, and the legs 13 have just passed a horizontal position, the anvil feet 26 and 27 move outward again to support legs 13, as shown in FIG. 8a. This freedom of the anvil feet 26 and 27 to splay and return toward original position during the course of deformation of the crown 12 of skin clip 11, i.e., the use of a pivot which does not restrain the lateral outward movement of the sections 24 and 25, results in a particularly desirable extraction pattern, as described previously, resulting in skin clip removal which is less traumatic to the patient.

The skin clip remover of this invention has been described in connection with a preferred embodiment, and modifications of such preferred embodiment have also been described, but it is understood that other modifications in structure can be made which do not alter the inventive features disclosed herein. The use in a skin clip remover of a hawk bill projection and associated structure to position properly and retains a skin clip for deformation and the use in a skin clip remover of a pivot which does not restrain the lateral outward movement of anvil feet under deforming load to better distribute the deforming load, taken singly or preferably in combination provides a skin clip remover capable of performing extractions of skin clips with less trauma to the patient.

What I claim is:

1. A skin clip remover comprising a handle element and a trigger element joined together intermediate their ends by a pivot, said handle element comprising a proximal end with manipulating means and a distal end divided logitudinally into two parallel sections terminating in two parallel anvil feet each formed at an obtuse angle both to top surface of associated parallel section and to longitudinal axis of said handle element, said trigger element comprising a proximal end with manipulating means and a distal end sized to fit between the two parallel sections of the distal end of said handle element and terminating in a hawk bill projection formed at an obtuse angle both to an approach surface and to longitudinal axis of said trigger element, said obtuse angle of the hawk bill projection arranged to oppose the obtuse angles of the anvil feet, the pivot joining the handle element and the trigger element permitting lateral outward movement at the pivot of each of the two parallel sections of the distal end of the handle element.

2. In a hand operated skin clip remover having two elements joined together by a pivot at a point intermediate their ends with one element split at its distal end to form two parallel anvil feet and the other element having a single member at its distal end sized to fit between said anvil feet when the proximal ends of two elements are brought toward each other to provide a hand operated tool capable of gripping an object between opposing faces of the distal ends of said two elements, the improvement which comprises providing the pivot in a form permitting lateral outward movement at the pivot of two sides of the split distal end of the one element.

* * * * *